United States Patent
Madhavi et al.

(10) Patent No.: US 7,297,803 B2
(45) Date of Patent: *Nov. 20, 2007

(54) PROCESS FOR THE PREPARATION OF LUTEIN ESTER CONCENTRATE

(75) Inventors: Doddabele L. Madhavi, Worcester, MA (US); Daniel I. Kagan, Belmont, MA (US)

(73) Assignee: BioActives, LLC, Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/348,141

(22) Filed: Feb. 6, 2006

(65) Prior Publication Data

US 2007/0185342 A1    Aug. 9, 2007

(51) Int. Cl.
*C07C 233/00* (2006.01)
(52) U.S. Cl. ........................................ 554/12
(58) Field of Classification Search ............ 554/12
See application file for complete search history.

(56) References Cited

U.S. PATENT DOCUMENTS

| 4,048,203 | A | 9/1977 | Philip |
| 6,191,293 | B1 | 2/2001 | Levy |
| 6,737,535 | B2 | 5/2004 | Kumar, T.K. |
| 2003/0130531 | A1 | 7/2003 | Sadano et al. |
| 2006/0020030 | A1 | 1/2006 | Ornelas-Cravioto et al. |

FOREIGN PATENT DOCUMENTS

WO    WO 02094772    11/2002

*Primary Examiner*—Deborah D. Carr
(74) *Attorney, Agent, or Firm*—Mueller Smith & Matto

(57) ABSTRACT

A method for concentrating trans-lutein esters from marigold oleoresin, which includes blending the oleoresin with a solvent and a co-solvent of lower alkanols and recovering a precipitate enriched with trans-lutein esters at a temperature of above 22° C. The recovery of the trans-lutein esters is greater using the alkanol blend than when using only a lower alkanol in the said blend. The process is most useful using a lower-grade, commercially available oleoresin, thereby helping small producers, who do not have access to higher-grade oleoresin made through backward integration to marigold cultivation and harvest.

8 Claims, No Drawings

PROCESS FOR THE PREPARATION OF LUTEIN ESTER CONCENTRATE

CROSS-REFERENCE TO RELATED APPLICATIONS

None

STATEMENT REGARDING FEDERALLY SPONSORED RESEARCH

Not applicable.

BACKGROUND OF THE INVENTION

The present invention relates to an improved process for the purification of lutein esters from commercially available marigold oleoresin.

Marigold oleoresin contains a variety carotenoids: phytoene, phytofluene, α-carotene, β-carotene, α-carotene, β-carotene, α-carotene, α-cryptoxanthin, β-cryptoxanthin, lutein, antheraxanthin, zeaxanthin, and neoxanthin. The xanthophyll esters in marigold oleoresin predominate in lutein fatty acid esters with varying proportions of the trans- and cis-lutein isomers. The cis-isomers are formed due to exposure of the raw materials to heat, oxygen, and light during processing. The purified lutein ester concentrate with a high proportion of trans-isomers is used in the nutritional supplement industry, such as by being formulated as oil dispersions and beadlets for capsules and tablets. The esters also are used as food colorants and in functional foods.

Unlike free lutein, the lutein ester concentrate is a less expensive ingredient in a highly competitive market. Hence, development of an economical, efficient process for purifying lutein esters has been the focus of a number of patents. In general, the purification of the esters involves use of organic solvent(s) to remove non-xanthophyll impurities, inactive cis-isomers of lutein and also to precipitate or crystallize the xanthophyll esters from the oleoresin. The solvents used generally are lower aliphatic alcohols or ketones. The objective of these publications is to purify the esters to 40% or above containing mainly the trans-lutein esters, suitable for human consumption.

One of the major disadvantages of these processes is the significant reduction in the recovery of the trans-lutein esters during the precipitation step as the esters are lost due to dissolution in the solvents used. Additionally, the processes either use solvents that require special high-cost extraction equipment or very high-quality oleoresin normally not available to small producers who are not backward integrated to the marigold harvest process.

In earlier publications and U.S. Pat. No. 4,048,203, Philip describes purification of the lutein esters by dissolving the oleoresin in lower aliphatic alcohols, preferably isopropanol at 75° C. followed by precipitation at 15° C. to obtain the esters at 51% purity. However, this heat treatment results in an undesirably large proportion of the less-bioavailable cis-lutein isomer in the final product as reported by Levy (U.S. Pat. No. 6,191,203).

Levy discloses a method in U.S. Pat. No. 6,191,293 for the preparation of a trans-lutein esters content at least four times greater and preferably at least nine times greater than the cis-lutein esters content. The lutein esters are extracted from marigold flowers by contacting the corollas with a hydrocarbon solvent. After solvent removal, the crude esters then are mixed with isopropanol at room temperature, preferably at 20° C. where they crystallize off, and the purified esters are collected by filtration. The process provides esters with 40% to 70% purity, but the recovery generally does not exceed 50%-60%. The raw material used also is more purified, as the oleoresin is prepared using corollas, instead of the whole flower head. In the commercial manufacture of the marigold oleoresin, the whole flower head is dried and extracted resulting in the oleoresin with a number of non-xanthophyll impurities. This enriched material is normally not available to small producers.

In order to improve the yield, Quesnel and Flacher (WO 02094772) have disclosed a method of pre-treating the marigold corollas with an alcohol or a nitrile solvent for a time sufficient to extract any non-xanthophyll compounds, followed by extraction of the remaining raw material with a hydrocarbon solvent for a sufficient time to extract the xanthophyll esters. The reported recovery was up to 100% with a purity of 54%-65%. The process, however, requires a change in the commercial production practices for the manufacturers of the marigold flower meal and the oleoresin, which, based on the market potential for the esters is not a practical option.

U.S. Pat. No. 6,737,535 discloses the use of aliphatic ketones for the purification of the commercially available marigold oleoresin. The oleoresin is admixed with the solvent at a ratio of 1:3 to 1:15 and stirred for preferably around 10 hr at a temperature in the range of 15°-30° C. The precipitated lutein esters are separated by filtration, washed with fresh solvent, and dried under vacuum at room temperature. The use of highly volatile solvents with long extraction time, filtration, and washing steps makes this process uneconomical and unattractive due to safety concerns and the need for increased capital expenditure for special extraction equipment.

U.S. Patent Publication 2003/0130531 discloses a multiple step process for the purification of the xanthophylls esters to not less than 70% purity. The oleoresin is dissolved in acetone at 50° C., cooled to 20° C. and the precipitated material is filtered off. The acetone is removed under reduced pressure to obtain an acetone soluble concentrate. The concentrate is further dissolved in n-butanol at 45° C., cooled to 4° C. to remove an n-butanol soluble impurity with or without the addition of water or lower alcohols such as methanol or ethanol. The precipitate is separated by filtration and mixed with excess of ethanol, dispersed and then separated by filtration, followed by drying under vacuum. The multiple steps involved make this process economically not feasible.

U.S. Patent Publication 2006/0020030 proposes a composition at least 81% of which by weight are xanthophyll esters of which at least 94% are trans-lutein esters. Such composition is made by mixing marigold oleoresin with a non-polar solvent, typified by ethanol. The use of highly volatile solvents and the low yield of the final product make this process uneconomical.

BRIEF SUMMARY OF THE INVENTION

The present invention describes an improved commercial method for the purification of trans-lutein esters from commercially available marigold oleoresin. This improvement is particularly attractive to small producers, who only have access to a lower-grade oleoresin. The process results in an improved recovery of about 70% to about 78% of the trans-lutein esters, while maintaining about 55% or more purity of the total esters. In the HPLC profile, the area percentage for trans-lutein was about 88% to about 92% in all the treatments. The ratio of trans-lutein:cis-lutein content was about 15:1 to about 40:1 in the purified esters in all the treatments as opposed to about 3:1 in the oleoresin.

The process uses a primary or secondary aliphatic alcohol blend with one of the lower alcohols functioning as a solvent modifier or a co-solvent to increase the precipitation of the trans-lutein esters at about room temperature. It was surprisingly found that the recovery of the esters could be significantly modulated by altering the amount of the solvent modifier in the mixture. Furthermore, the entire process can be carried out at a temperature ranging from about 22° C. to about 28° C., and includes the steps of admixing the solvents with the oleoresin to dissolve the non-xanthophyll impurities, filtering to separate the precipitated esters, and drying under vacuum at about 30° C. The solvents can be recovered and recycled.

DETAILED DESCRIPTION OF THE INVENTION

The invention is a commercial method for the purification of lutein esters from commercially available marigold oleoresin. Food grade marigold oleoresin produced, for example, by hexane extraction of whole flower heads was used for the studies. The oleoresin typically contains about 20% or less of total xanthophyll esters (as opposed to about 27% in the high-grade oleoresin extracted from petals alone), about 71%-75% trans-lutein, and about 23%-25% cis-lutein. The oleoresin also contains a number of non-carotenoid impurities, such as, for example, triglycerides, polar pigments, sterols, and resins. The composition of these impurities varies depending on, inter alia, the crop, cultivation practices, soil, and seasonal variations.

A basic tenet of the invention is the use of isopropanol or n-propanol as a solvent with ethanol as a cosolvent to improve the recovery of trans-lutein esters while retaining the purity above about 55%. At 22° C. or higher, a portion of the trans-lutein esters remains soluble in the solvent and the recovery in the precipitate is reduced. By adding ethanol co-solvent, we can sufficiently weaken the solvating power of the isopropanol or n-propanol solvent, so that more of the trans-lutein esters precipitate out at room temperature.

While butanol will function as a solvent for the concentration of lutein esters from oleoresin, higher alcohols having higher boiling points that makes solvent separation and recovery more difficult and higher alcohols have toxicity issues. Thus, lower alkanols, for present purposes are $C_1$ to $C_4$ alcohols with $C_1$ to $C_3$ alcohols being commercially more significant. Broad, however, any alkanol that will dissolve oleoresin impurities for the concentration of lutein esters and can be separated from the lutein ester concentrate is suitable for use in the present process. The cosolvent desirably will be a poorer solvent for the oleoresin than the solvent; thus, the use of ethanol as the cosolvent. Quite surprisingly, ethanol cosolvent improves the amount of trans-lutein esters in the precipitate without reducing the temperature of the mixture and does not increase unwanted impurities in the precipitate. Purity and yield, then, both increase using the inventive process.

In an initial study, the lutein esters were precipitated at about 22°-28° C. using the three lower alcohols—isopropanol, n-propanol and, ethanol—for 3-5 hours. The solvent to oleoresin ratio was between about 2:1 to 5:1. The extracts were filtered under vacuum and the precipitate was dried under vacuum at 30° C. Surprising, the three alcohols significantly affected the recovery of the trans-lutein esters. The recovery of trans-lutein esters and purity of the total carotenoids were:

| Solvent | % Recovery | % Purity |
| --- | --- | --- |
| n-Propanol | 64 | 62 |
| Isopropanol | 62 | 60.5 |
| Ethanol | 95 | 35 |

The precipitates from isopropanol and from n-propanol were dry and could be powdered after drying, whereas ethanol resulted in an oily paste.

The temperature at which the precipitation was carried out also was important in determining the purity of the esters. At temperatures lower than about 22° C., some of the impurities in the oleoresin started to precipitate out with the esters, resulting in a sticky paste with lower purity. Also, when oleoresin in isopropanol was heated to 75° C. and cooled to 15° C., a significant amount of the oleoresin, nearly 60%, precipitated out of solution.

Based on these studies, conditions to increase the recovery of the trans-lutein esters at about 22° C. and above were explored. Since ethanol was the weakest of the three alcohols in dissolving the lutein esters, the effect of admixing various amounts of ethanol from about 10%-50% (v/v) to isopropanol or n-propanol on the recovery of trans-lutein esters and purity of the esters was tested. Again unexpectedly, isopropanol was determined to be very sensitive to increasing concentrations of ethanol, as compared to n-propanol. There was an increase in the recovery of trans-lutein esters to about 70%-80% with increasing concentrations of ethanol (which is not a good solvent by itself) in isopropanol, while the purity ranged between about 56%-60%. In the HPLC profile, the area percentage for trans-lutein was about 88%-92% in all the treatments. The ratio of trans-lutein:cis-lutein content was between about 15:1 to about 40:1 in the purified esters in all the treatments, as opposed to about 3:1 in the oleoresin. With n-propanol, increasing the ethanol concentration to about 50% resulted in about a 73% recovery of trans-lutein esters with a purity of about 58%. The results clearly show that ethanol can be used as a solvent modifier or co-solvent to improve the yield of the esters.

The following examples show how the present invention has been practiced, but they should not be construed as limiting. In this application all units are in the metric system and all amounts and percentages are by weight, unless otherwise expressly indicated.

IN THE EXAMPLES

In the examples, the total carotenoid ester content was determined by spectrophotometry. Each sample was dissolved in hexane:ethyl acetate (1:1) to form a 1 mg/ml solution under sonication. The solution was diluted 1:100 with hexane and the absorbance determined at 445 nm. The carotenoid ester content, as lutein, was determined using an E1% of 1394 (Davies, Carotenoids, *In Chemistry and Biochemistry of Plant Pigments*, Ed: Goodwin, Academic Press, London, 1976). The ratio of trans-:cis-lutein content was determined after hydrolyzing the esters and determining the area percentages of trans-lutein and cis-lutein by HPLC.

Example 1

Marigold oleoresin containing 20% total carotenoids showing 71% trans-lutein isomers and 23% cis-lutein isomers by HPLC area percentages was used for the studies. Isopropanol and ethanol were combined in different proportions (v/v), 100% isopropanol/0% ethanol; 90% isopropanol/10% ethanol; 80% isopropanol/20% ethanol; and 70% isopropanol/30% ethanol. One hundred grams of the oleoresin was used for extraction with each solvent combination. The oleoresin was mixed with 300 ml of the solvent and stirred at 23°-26° C. for four hours. The precipitate was separated by vacuum filtration, any leftover solution was washed with fresh solvent, and the precipitate was dried under vacuum at 30° C. The purity was determined by spectrophotometry, as described before. The ratio of trans-lutein:cis-lutein ester content was determined by area percentage in the HPLC profile. The recovery and purity are presented in Table 1.

TABLE 1

| Solvent | Yield (g) | Purity of total carotenoids (% w/w) | Recovery of trans-Lutein Esters (% of amount in 100 g oleoresin) |
|---|---|---|---|
| Isopropanol 100% | 16.00 | 60.58 | 62 |
| Isopropanol:ethanol 90:10 | 18.10 | 60.79 | 71 |
| Isopropanol:ethanol 80:20 | 21.20 | 56.63 | 76 |
| Isopropanol:ethanol 70:30 | 22.30 | 56.55 | 78 |

It was found that even at 30% ethanol concentration, the solvent composition selectively precipitated the trans-lutein esters. The area percentage for trans-lutein ranged from between 88% and about 92% in the treatments. The ratio of trans-lutein:cis-lutein content ranged between about 15:1 and about 40:1 in the purified esters as opposed to 3:1 in the oleoresin. The recovery of trans-lutein esters was calculated based on the amount of trans-lutein esters in the oleoresin.

Example 2

One hundred grams of marigold oleoresin containing 20% total carotenoids showing 71% trans-lutein isomers and 23% cis-lutein isomers by HPLC area percentages was processed with 100% n-propanol and n-propanol (50%):ethanol (50%) as described in Example 1. Both treatments resulted in a higher trans-lutein to cis-lutein ratio (42:1 for 100% n-propanol; 32:1 for n-propanol:ethanol at a ratio of 1:1). The recovery and purity were calculated as described before. The results are presented in Table 2.

TABLE 2

| Solvent | Yield (g) | Purity of total carotenoids (% w/w) | Recovery of trans-Lutein Esters (% of amount in 100 g oleoresin) |
|---|---|---|---|
| n-Propanol 100% | 16.00 | 62.00 | 64 |
| n-Propanol:ethanol 50:50 | 19.50 | 58.26 | 73 |

While the invention has been described with reference to various embodiments, those skilled in the art will understand that various changes may be made and equivalents may be substituted for elements thereof without departing from the scope and essence of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. In this application, all citations referred herein are expressly incorporated herein by reference.

We claim:

1. In a method for concentrating trans-lutein esters from marigold oleoresin by blending a solvent therewith and recovering a precipitate enriched with trans-lutein esters, the improvement which comprises the steps of:
   (a) blending said marigold oleoresin with a mixture of ethanol and a propanol lower alkanols at a temperature of above about 22° C. to form a blend; and
   (b) recovering a trans-lutein ester concentrate from said blend, wherein the recovery of the trans-lutein ester content of said concentrate is greater than when using only a lower alkanol in said blend.

2. The improved method of claim 1, wherein mixture of ethanol and a propanol is one or more of isopropanol/ethanol or n-propanol/ethanol.

3. The improved method of claim 1, wherein step (a) is conducted at a temperature ranging from about 22° C. to 28° C.

4. The improved method of claim 1, wherein step (b) includes filtering to separate the trans-lutein ester concentrate, and drying under vacuum at about 30° C.

5. The improved method of claim 1, wherein said solvent mixture in step (b) is recovered and recycled to step (a).

6. The improved method of claim 1, wherein the ratio of said marigold oleoresin to said mixture of ethanol and a propanol ranges from about 1:5 to about 1:2 (w/v).

7. The improved method of claim 1, wherein said marigold oleoresin is an extract product of the entire marigold flower.

8. The improved method of claim 7, wherein said marigold oleoresin contains about 20% or less total carotenoids.

* * * * *